(12) United States Patent
Ghose et al.

(10) Patent No.: US 11,699,522 B2
(45) Date of Patent: Jul. 11, 2023

(54) UNIFIED PLATFORM FOR DOMAIN ADAPTABLE HUMAN BEHAVIOUR INFERENCE

(71) Applicant: Tata Consultancy Services Limited, Mumbai (IN)

(72) Inventors: Avik Ghose, Kolkata (IN); Arijit Chowdhury, Kolkata (IN); Sakyajit Bhattacharya, Kolkata (IN); Vivek Chandel, Gurgaon (IN); Arpan Pal, Kolkata (IN); Soma Bandyopadhyay, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1011 days.

(21) Appl. No.: 16/396,276

(22) Filed: Apr. 26, 2019

(65) Prior Publication Data

US 2019/0332950 A1 Oct. 31, 2019

(30) Foreign Application Priority Data

Apr. 27, 2018 (IN) .............................. 201821016084

(51) Int. Cl.
*G06N 5/02* (2023.01)
*G06N 5/04* (2023.01)
(Continued)

(52) U.S. Cl.
CPC ........... *G16H 40/67* (2018.01); *A61B 5/7275* (2013.01); *G06F 16/908* (2019.01);
(Continued)

(58) Field of Classification Search
CPC ........ G06N 5/022; G06N 5/04; A61B 5/7275; G06F 16/9035; G06F 16/908; G06K 9/6289; G16H 40/67
See application file for complete search history.

(56) References Cited

U.S. PATENT DOCUMENTS

2014/0361905 A1* 12/2014 Sadasivam ............. G08C 17/02
340/870.01
2015/0067176 A1* 3/2015 Dubois ............... H04L 65/1073
709/227
(Continued)

OTHER PUBLICATIONS

Ahlberg, J. et al. (2008). "Prometheus: Prediction and interpretation of human behavior based on probabilistic structures and heterogeneous sensors," *European Coordinating Committee for Artificial Intelligence (ECCAI)*, 2 pages.
(Continued)

*Primary Examiner* — Hosain T Alam
*Assistant Examiner* — Chongsuh Park
(74) *Attorney, Agent, or Firm* — Finnegan, Henderson, Farabow, Garrett & Dunner LLP

(57) ABSTRACT

This disclosure relates generally to a unified platform for domain adaptable human behaviour inference. The platform provides a unified, low level inference and high level inference of domain adaptable human behaviour inference. The low level inferences include cross-sectional analysis techniques to infer location, activity, physiology. Further the high inference that provide useful and actionable for longitudinal tracking, prediction and anomaly detection is performed based on several longitudinal analysis techniques that include welch analysis, cross-spectrum analysis, Feature of interest (FOI) identification and time-series clustering, autocorrelation-based distance estimation and exponential smoothing, seasonal and non-seasonal models identification, ARIMA modelling, Hidden Markov models, Long short term memory (LSTM) along with low level inference, human meta-data and application domain knowledge. Further the unified human behaviour inference can be obtained across multiple domains that include health, retail and transportation.

9 Claims, 7 Drawing Sheets

(51) Int. Cl.
  *G06K 9/62* (2022.01)
  *G06F 16/9035* (2019.01)
  *A61B 5/00* (2006.01)
  *G16H 40/67* (2018.01)
  *G06F 16/908* (2019.01)
  *G06N 5/022* (2023.01)
  *G06F 18/25* (2023.01)

(52) U.S. Cl.
  CPC ........ *G06F 16/9035* (2019.01); *G06F 18/251* (2023.01); *G06N 5/022* (2013.01); *G06N 5/04* (2013.01)

(56) References Cited

U.S. PATENT DOCUMENTS

| | | |
|---|---|---|
| 2015/0313529 A1 | 11/2015 | Nevo et al. |
| 2017/0024660 A1 | 1/2017 | Chen et al. |
| 2017/0164878 A1* | 6/2017 | Connor ................. G09B 19/00 |
| 2018/0341706 A1* | 11/2018 | Agrawal .............. G06V 20/597 |

OTHER PUBLICATIONS

Almeida, A. et al. (Dec. 2017). "Predicting Human Behaviour with Recurrent Neural Networks," *Applied Sciences*, vol. 8, No. 2; pp. 1-13.

* cited by examiner

| Use Case | Sensors | Low level inference | High level inference |
|---|---|---|---|
| Early MCI detection in ambient assisted living | PIR sensors, door contact and pill-box sensors | Daily and weekly routine | Mild cognitive impairment |

FIG. 4

| Use Case | Sensors | Low level inference | High level inference |
|---|---|---|---|
| Driver behaviour modelling | GPS, inertial sensors | Location, speed, lateral velocity, jerk | Harsh driving events |

FIG. 5

| Use Case | Sensors | Low level inference | High level inference |
|---|---|---|---|
| Cardiac fatigue monitoring | Accelerometer, gyroscope, barometer, PPG sensors. | Metabolic Equivalents (MET) values, heart rate, breathing-rate, breathing power | Computational model of cardiac fatigue per session of activity, cardiac care. |

FIG. 6

| Use Case | Sensors | Low level inference | High level inference |
|---|---|---|---|
| Ubiquitous Journey recognition | GPS, Accelerometer, gyroscope, barometer, magnetometer. | Type of vehicle recognition | Journey recognition |

FIG. 7

UNIFIED PLATFORM FOR DOMAIN ADAPTABLE HUMAN BEHAVIOUR INFERENCE

PRIORITY CLAIM

This U.S. patent application claims priority under 35 U.S.C. § 119 to: India Application No. 201821016084, filed on Apr. 27, 2018. The entire contents of the aforementioned application are incorporated herein by reference.

TECHNICAL FIELD

This disclosure relates generally relates to field of human behaviour inference and, more particularly, a unified platform for domain adaptable human behaviour inference.

BACKGROUND

Human Information Interaction (HII) investigate human behaviour that involves an inference of how humans deal with their surroundings including other humans, with focus on people's relationship with information, rather than with technology. Further the human behaviour cannot be treated as a pure reactive system which only responds to a stimuli, but rather as a hybrid system which both seeks and assimilates information.

The HII techniques that involves inference of human interaction over time along with situation/environment based context for prediction of human activity has multiple applications in cyber as well as the physical world for various domains like elderly health care, ergonomics, and worker's safety and so on. The HII captures mental state, physical body conditions, lifestyle, and location of individuals to infer various human behaviour patterns including physiological, emotive, functional sensing, and location analysis.

The existing behaviour analysis frameworks provide robust framework for machine-to-machine architecture, however there are very few dedicated frameworks for efficient human sensing applications. Among the few existing human context sensing applications, the sensing framework is mostly generic and does not mostly include nuances of human sensing, nor can it be applied across multiple domains. Further, few other existing human behaviour inference applications are mostly independent separate entities that limited to mobile phones and does not include other sensors like wearable, infrastructure and near field sensors.

SUMMARY

Embodiments of the present disclosure present technological improvements as solutions to one or more of the above-mentioned technical problems recognized by the inventors in conventional systems. For example, in one embodiment, a unified platform for domain adaptable human behaviour inference is provided. The platform provides a domain adaptable human behaviour unified inference that includes low level inference and high level inference. The low level inferences include cross-sectional analysis techniques to infer location, activity, physiology. Further the high inference that provide useful and actionable for longitudinal tracking, prediction and anomaly detection is performed based on several longitudinal analysis techniques that include welch analysis, cross-spectrum analysis, Feature of interest (FOI) identification and time-series clustering, autocorrelation-based distance estimation and exponential smoothing, seasonal and non-seasonal models identification, ARIMA modelling, Hidden Markov models, Long short term memory (LSTM) along with low level inference, human meta-data and application domain knowledge. Further the unified human behaviour inference can be obtained across multiple domains that include health, retail and transportation.

In another aspect, a method for obtaining a unified platform for domain adaptable human behaviour inference is provided. The method includes receiving a plurality of sensor data using a plurality of sensors, wherein the plurality of sensor data is in more than one sensor data formats. Further the method includes processing the received sensor data to a standard format. Further the method includes analyzing the processed sensor data using cross-sectional analysis to obtain low level inference. Further the method includes analyzing the processed sensor data using a plurality of longitudinal analysis and fourier analysis techniques based on the low level inference, domain knowledge and standard human metadata. Further the method includes selecting a longitudinal analysis technique from the plurality of longitudinal analysis techniques for obtaining high level inference, wherein the longitudinal analysis technique is selected based on expectation maximization techniques. Further the method includes obtaining the human behavior inference based on the obtained low level inference and the high level inference.

In another aspect, a system for a unified platform for domain adaptable human behaviour inference is provided. The system comprises a memory storing instructions and a centralized database, one or more communication interfaces; and one or more hardware processors coupled to the memory via the one or more communication interfaces, wherein the one or more hardware processors are configured by instructions to includes an input module configured for receiving a plurality of sensor data using a plurality of sensors, wherein the plurality of sensor data is in more than one sensor data formats. Further the system comprises a pre-processor configured for processing the received sensor data to a standard format. Further the system comprises a low level inference module configured for analyzing the processed sensor data using cross-sectional analysis to obtain low level inference. Further the system comprises a high level inference module configured for analyzing the processed sensor data using a plurality of longitudinal analysis and fourier analysis techniques based on the low level inference, domain knowledge and standard human metadata and selecting a longitudinal analysis technique from the plurality of longitudinal analysis techniques for obtaining high level inference, wherein the longitudinal analysis technique is selected based on expectation maximization techniques. The high level inference module is connected to a domain database and a human metadata database, wherein the domain database configured for saving and dynamically updating domain knowledge including exhaustive domain knowledge of health, shopping, retail and driving, while the human metadata database for saving and dynamically updating standard human metadata including mobility, proximity, activity for standard human. The high level inference module further comprises a domain adaptation module, an observation adaption module, a core inference module, a human meta-data and grouping module, a human knowledge module, a core inference module and a output module. The system further comprises a unified display module configured for displaying the obtained human behavior inference based on the obtained low level inference and the high level inference.

In yet another aspect, a non-transitory computer readable medium to obtain a unified platform for domain adaptable human behaviour inference is provided. The program includes receiving a plurality of sensor data using a plurality of sensors, wherein the plurality of sensor data is in more than one sensor data formats. Further the program includes processing the received sensor data to a standard format. Further the program includes analyzing the processed sensor data using cross-sectional analysis to obtain low level inference. Further the method includes analyzing the processed sensor data using a plurality of longitudinal analysis and Fourier analysis techniques based on the low level inference, domain knowledge and standard human metadata. Further the program includes selecting a longitudinal analysis technique from the plurality of longitudinal analysis techniques for obtaining high level inference, wherein the longitudinal analysis technique is selected based on expectation maximization techniques. Further the program includes obtaining the human behavior inference based on the obtained low level inference and the high level inference.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 4 illustrates a use case example of ambient assisted living for geriatric subjects for domain adaptable human behaviour inference using the unified platform, according to some embodiments of the present disclosure.

FIG. 5 illustrates a use case example of driving behavior understanding for smart transportation for domain adaptable human behaviour inference using the unified platform, according to some embodiments of the present disclosure.

FIG. 6 illustrates a use case example of cardiac care pathway for patients with uncontrolled hypertension for domain adaptable human behaviour inference using the unified platform, according to some embodiments of the present disclosure.

FIG. 7 illustrates a use case example of ubiquitous journey recognition for domain adaptable human behaviour inference using the unified platform, according to some embodiments of the present disclosure.

DETAILED DESCRIPTION

Figure 1:
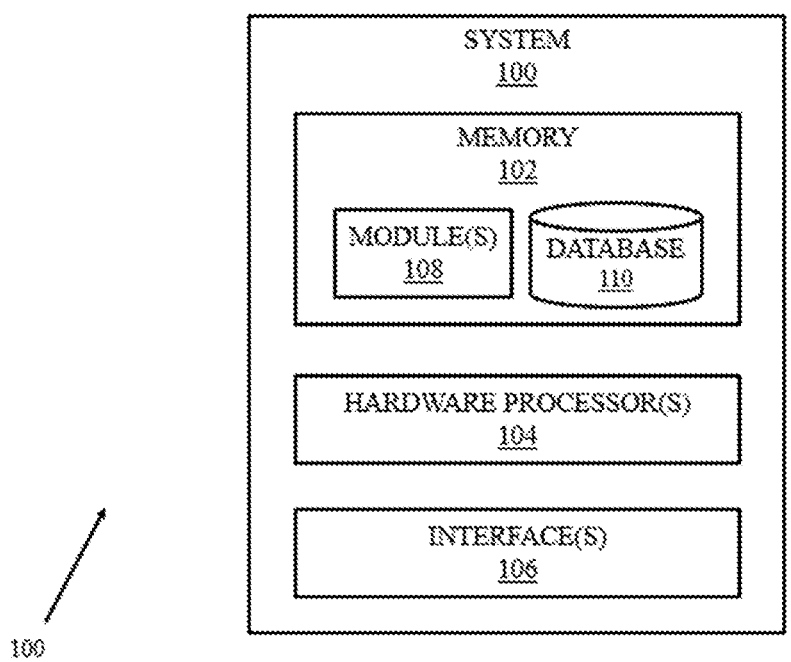
FIG. 1 illustrates an exemplary block diagram of a unified platform for domain adaptable human behaviour inference with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIG. 1 through FIG. 7, where similar reference characters denote corresponding features consistently throughout the figures, there are shown preferred embodiments and these embodiments are described in the context of the following exemplary system and/or method.

FIG. 1 illustrates an exemplary block diagram of a system (100) for domain adaptable human behaviour inference according to an embodiment of the present disclosure. The system (100) is provided as a unified platform as it provides a domain adaptable unified inference of low level inference and high level inference of human behaviour. In an embodiment, the system 100 includes memory 102, one or more hardware processors (104), communication interface device (s) or input/output (I/O) interface(s) (106), and one or more data storage devices or memory (102) operatively coupled to the one or more processors (104). The memory (102) comprises one or more modules (108) and the database (110). The one or more processors (104) that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system (100) can be implemented in a variety of computing systems, such as laptop computers, notebooks, hand-held devices, workstations, mainframe computers, servers, a network cloud and the like.

The I/O interface device(s) (106) can include a variety of software and hardware interfaces, for example, a web interface, a graphical subject interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory (102) may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

Figure 2:
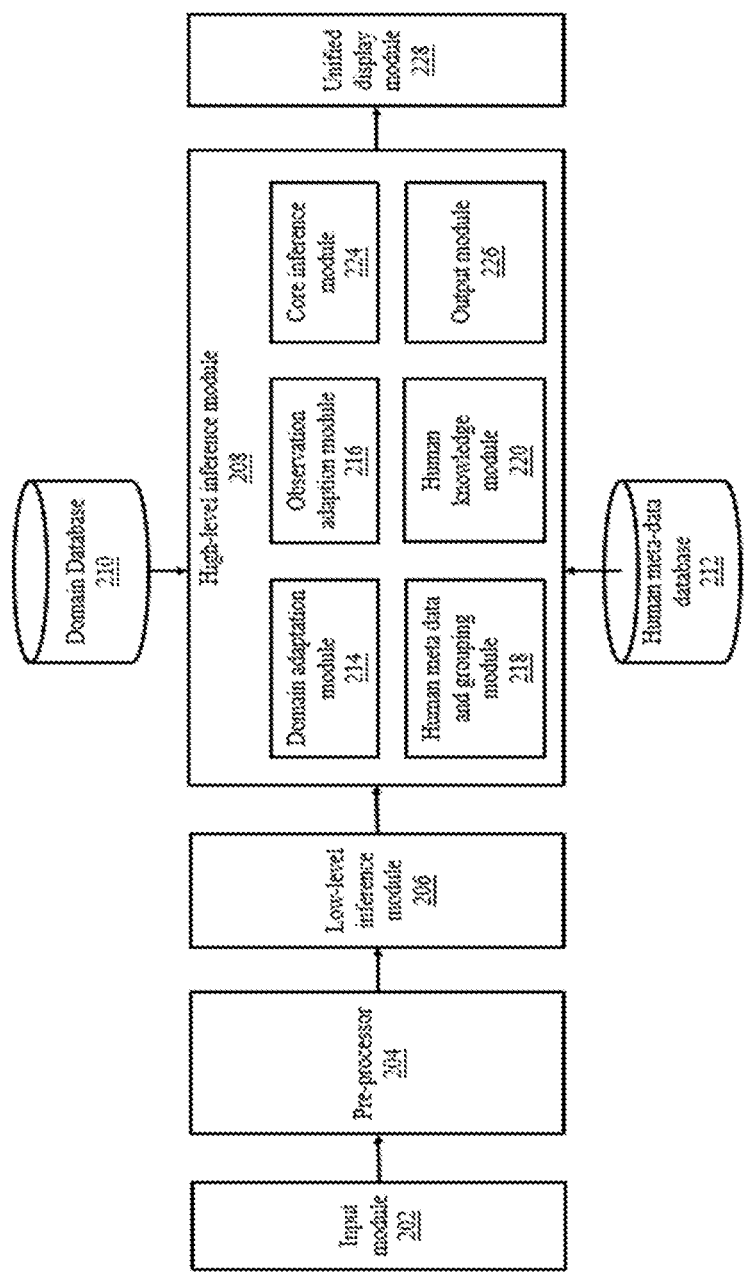
FIG. 2 is a functional block diagram of various modules stored in module(s) of a memory of the system of FIG. 1 in accordance with some embodiments of the present disclosure.

FIG. 2, with reference to FIG. 1, is a block diagram of various modules 108 stored in the memory (102) of the system 100 of FIG. 1 in accordance with an embodiment of the present disclosure. In an embodiment of the present disclosure, the system (100), comprises an input module (202) configured for receiving a plurality of sensor data using a plurality of sensors, wherein the plurality of sensor data is in more than one sensor data formats. Further the system 100 comprises a pre-processor (204) configured for processing the received sensor data to a standard format. Further the system 100 comprises a low level inference module (206) configured for analyzing the processed sensor data using cross-sectional analysis to obtain low level inference. Further the system (100) comprises a high level inference module (208) configured for analyzing the processed sensor data using a plurality of longitudinal analysis and fourier analysis techniques based on the low level inference, domain knowledge and standard human metadata and selecting a longitudinal analysis technique from the plurality of longitudinal analysis techniques for obtaining high level inference, wherein the longitudinal analysis technique is selected based on expectation maximization techniques. The high level inference module (208) is connected to a domain database (210) and a human metadata database (212), wherein the domain database (210) configured for saving and dynamically updating domain knowledge including exhaustive domain knowledge of health, shopping, retail and driving, while the human metadata database (212) for saving and dynamically updating standard human metadata including mobility, proximity, activity for standard human. The high level inference module (208) further comprises a domain adaptation module (214), an observation adaption module (216), a core inference module (224), a human meta-data and grouping module (218), a human knowledge module (220), a core inference module (224) and an output module (226). The system 100 further comprises a unified display module (228) configured for displaying the obtained human behavior inference based on the obtained low level inference and the high level inference that are implemented as at least one of a logically self-contained part of a software program, a self-contained hardware component, and/or, a self-contained hardware component with a logically self-contained part of a software program embedded into each of the hardware component that when executed perform the above method described herein.

According to an embodiment of the disclosure, the system (100) comprises the input module (202) configured for receiving a plurality of sensor data using a plurality of sensors, wherein the plurality of sensor data is in more than one sensor data formats. In an embodiment, the plurality of personal sensors includes wearable sensors that include smart watches, infrastructure sensors that includes sensors embedded in infrastructures, near field sensors that include low-power ultrasound sensors, passive radio-frequency identification (RFID), infrared sensors, near-field communication (NFC) sensors and soft sensors that include databases with exhaustive details regarding the users.

According to an embodiment of the disclosure, the system (100) further comprises the pre-processor (204) configured for processing the received sensor data to a standard format. Since plurality of sensor data is received in more than one sensor data formats, the varying sensor formats are processed to a standard format that includes time series format. In an embodiment, processing the received sensor data to the standard format comprises time series format using linear, non-linear interpolation and phase removing filters.

According to an embodiment of the disclosure, the system (100) further comprises the low level inference module (206) configured for analyzing the processed sensor data using cross-sectional analysis techniques to obtain low level inference. The cross-sectional analysis for low level inference includes inferring or analyzing details such as location, activity, temperature and physiology based on observation of the pre-processed sensor data.

According to an embodiment of the disclosure, the system (100) further comprises the comprises a high level inference module (208) configured for analyzing the processed sensor data using a plurality of longitudinal analysis and fourier analysis techniques based on the low level inference, domain knowledge and standard human metadata and selecting a longitudinal analysis technique from the plurality of longitudinal analysis techniques for obtaining high level inference, wherein the longitudinal analysis technique is selected based on expectation maximization techniques.

The high level inference module (208) is connected to the domain database (210) and the human metadata database (212), wherein the domain database (210) configured for saving and dynamically updating domain knowledge including exhaustive domain knowledge of health, shopping, retail and driving, while the human metadata database (212) for saving and dynamically updating standard human metadata including mobility, proximity, activity for standard human.

The high level inference module (208) in the system (100), further comprises the domain adaptation module (214), the observation adaption module (216), the human meta-data and grouping module (218), the human knowledge module (220), the core inference module (224) and the output module (226).

The domain adaptation module (214) is configured to provide interoperability between low level inference module (206) and high level inference module (208) to standardize the variety of pre-processed sensor data of different semantics and syntax. Further the observation adaption module (216) is configured to provide interoperability between high level inference module (208) and domain database (210). Further the human meta-data and grouping module (218) comprises human Meta information like age, income-group, gender, geo-location can be used to group them into cohorts for aggregate level analytics, as an interface between high level inference module (208) and human meta-data database (212). Further the human knowledge module (220) is a repository that includes human constraints with respect to mobility, proximity and activity, where in a use case example, a human cannot run at 100 kmph speed. Further the core inference module (224) inputs from all other layers to take a final decision. Further the output module (226) is configured to a set of API/service for user applications to interface with the unified platform to further connect with unified display module (228) to display the unified human behavior inference.

According to an embodiment of the disclosure, the system (100) further comprises unified display module (228) configured for displaying the obtained human behavior inference based on the obtained low level inference and the high level inference. The platform provides a unified, low level inference and high level inference of domain adaptable human behaviour inference. The unified human behaviour inference is displayed on a unified display module (228) based on a user query, wherein low level inference or high level inference or both low level inference and the high level inference are displayed based on user query.

Figure 3:
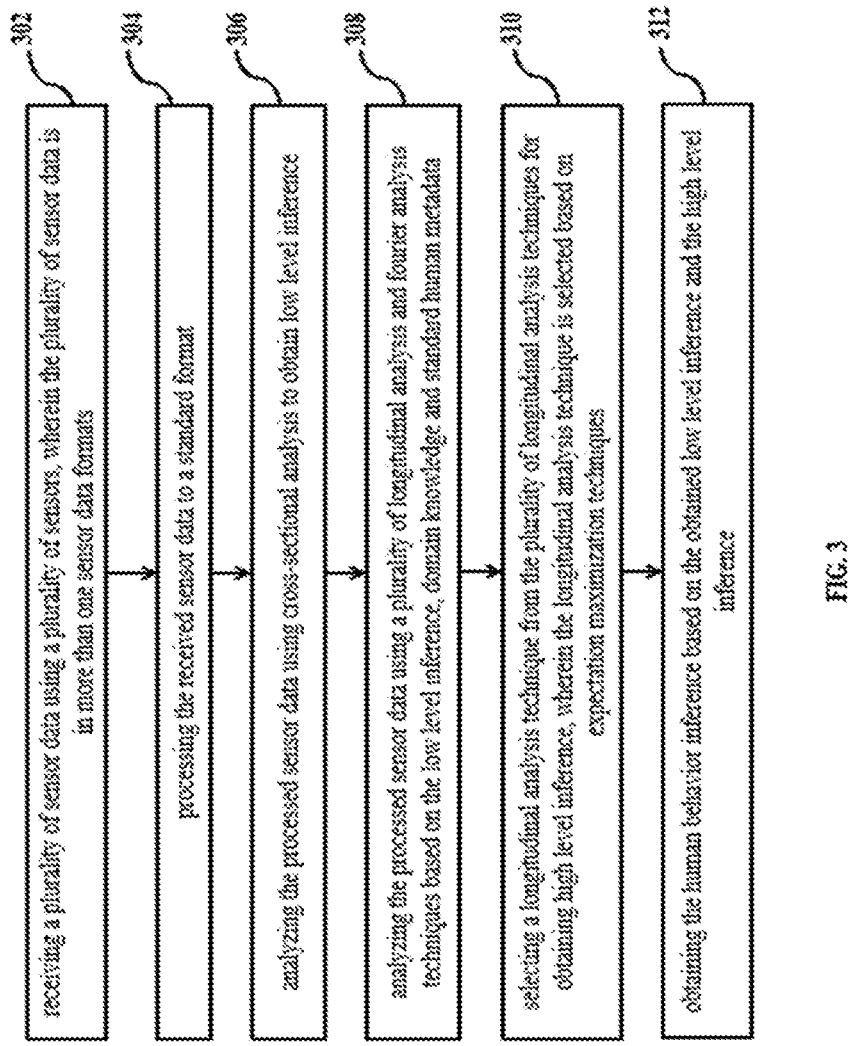
FIG. 3 is an exemplary flow diagram illustrating a method for a unified platform for domain adaptable human behaviour inference using the system of FIG. 1 in accordance with some embodiments of the present disclosure.

FIG. 3, with reference to FIGS. 1-2, is an exemplary flow diagram illustrating a method for obtaining domain adaptable human behaviour inference using a unified platform of the system 100 of FIG. 1 according to an embodiment of the present disclosure. In an embodiment, the system (100) comprises one or more data storage devices or the memory (102) operatively coupled to the one or more hardware processors (104) and is configured to store instructions for execution of steps of the method by the one or more processors (104). The steps of the method (300) of the present disclosure will now be explained with reference to the components of the system 100 and the modules 202-228 as depicted in FIGS. 1-2, and the flow diagram as depicted in FIG. 3.

At step 302, a plurality of sensor data is received using a plurality of sensors in the input module (202), wherein the plurality of sensor data is in more than one sensor data formats. The plurality of personal sensors includes wearable such as smart watch, infrastructure sensors that includes sensors embedded in infrastructures, near field sensors that include low-power ultrasound sensors, passive radio-frequency identification (RFID), infrared sensors, near-field communication (NFC) sensors and soft sensors that include databases with exhaustive details regarding the users.

At step 304, the received sensor data is processed to a standard format in the pre-processor (204). Since plurality of sensor data is received in more than one sensor data formats, the varying sensor formats are processed to a standard format that includes time series format. In an embodiment, processing the received sensor data to the standard format comprises time series format using linear, non-linear interpolation and phase removing filters.

In the next step at 306, the processed sensor data is analyzed using cross-sectional analysis to obtain low level inference in the low level inference module (206). The cross-sectional analysis for low level inference includes analyzing details such as location, activity, temperature and physiology.

In the next step at 308, the processed sensor data is analyzed using a plurality of longitudinal analysis and Fourier analysis techniques based on the low level inference, domain knowledge and standard human metadata in the high level inference module (208). The plurality of longitudinal analysis and fourier analysis techniques includes welch analysis, cross-spectrum analysis, Feature of interest (FOI) identification and time-series clustering, autocorrelation-based distance estimation and exponential smoothing, seasonal & non-seasonal models identification, ARIMA modelling, Hidden Markov models, Long short term memory (LSTM).

In the next step at 310, a longitudinal analysis technique is selected from the plurality of longitudinal analysis techniques for obtaining high level inference, wherein the longitudinal analysis technique is selected based on expectation maximization techniques in the high level inference module (208).

In the next step at 312, the human behavior inference based on the obtained low level inference and the high level inference is displayed in the unified display module (228). The unified human behavior inference is displayed as only low level inference or only high level inference or both low level inference and the high level inference are displayed based on user query.

FIG. 4 illustrates a use case example of ambient assisted living for geriatric subjects for domain adaptable human behaviour inference using the unified platform, according to some embodiments of the present disclosure. The plurality of sensors used for receiving driver related data include passive infrared (PIR) sensors, door contact and pill-box sensors. The received plurality of sensor data is pre-processed to a time series format. Further low-level inference is drawn that includes daily and weekly routine of geriatric subjects. Further based on low daily and weekly routine along domain knowledge and standard human metadata the high-level inference such as "Mild cognitive impairment detection among geriatric subjects" are inferred and displayed to user, based on user query for either low inference or high inference.

FIG. 5 illustrates a use case example of driving behavior understanding for smart transportation for domain adaptable human behaviour inference using the unified platform, according to some embodiments of the present disclosure. The plurality of sensors used for receiving driver related data include Global Positioning System (GPS), inertial sensors. The received plurality of sensor data is pre-processed to a time series format. Further low-level inference is drawn that includes location, speed, lateral velocity and jerk. Further based on low level inference (lateral velocity and jerk) along domain knowledge and standard human metadata the high-level inference such as "rash driving details" are inferred and displayed to user, based on user query, wherein if the user queries if the driver is driving rash, then the system displays in confirmation along with lateral velocity and jerk details.

FIG. 6 illustrates a use case example of cardiac care pathway for patients with uncontrolled hypertension for domain adaptable human behaviour inference using the unified platform, according to some embodiments of the present disclosure. The plurality of sensors used for receiving driver related data include Accelerometer, gyroscope, barometer, photoplethysmograph (PPG) sensors. The received plurality of sensor data is pre-processed to a time series format. Further low-level inference is drawn that includes Metabolic Equivalents (MET) values, heart rate, breathing-rate, breathing power. Further based on Metabolic Equivalents (MET) values, heart rate, breathing-rate, breathing power the high-level inference such as "Computational model of cardiac fatigue per session of activity" or "cardiac care." are inferred and displayed to user, based on user query for either low inference or high inference.

FIG. 7 illustrates a use case example of ubiquitous journey recognition for domain adaptable human behaviour inference using the unified platform, according to some embodiments of the present disclosure. The plurality of sensors used for receiving driver related data include photoplethysmograph (PPG), Accelerometer, gyroscope, barometer, photoplethysmograph (PPG) sensors. The received plurality of sensor data is pre-processed to a time series format. Further low-level inference is drawn that includes vehicle recognition. Further based on vehicle recognition the high-level inference such as "ubiquitous journey recognition" are inferred and displayed to user, based on user query for either low inference or high inference.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Hence a unified platform for domain adaptable human behaviour inference is provided. The platform provides a unified low level inference and high level inference of domain adaptable human behaviour inference. The low level inferences include cross-sectional analysis techniques to infer location, activity, physiology. Further the high inference uses several longitudinal analysis techniques that include welch analysis, cross-spectrum analysis, Feature of interest (FOI) identification and time-series clustering, autocorrelation-based distance estimation and exponential smoothing, seasonal and non-seasonal models identification, ARIMA modelling, Hidden Markov models, Long short term memory (LSTM along with low level inference, human meta-data and application domain knowledge to provide useful and actionable insights for longitudinal tracking, prediction and anomaly detection. Further the human behaviour inference can be obtained across multiple domains that include health, retail and transportation.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method for obtaining unified domain adaptable human behaviour inference using a unified platform, the method comprising:

receiving a plurality of sensor data using a plurality of sensors, wherein the plurality of sensor data is in one or more sensor data formats, wherein the plurality of sensors includes wearable sensors, infrastructure sensors, near field sensors, infrared sensors, Near-Field Communication (NFC) sensors and soft sensors and wherein the plurality of sensors comprises databases comprising details regarding one or more users;

processing the received plurality of sensor data to a time-series format;

analyzing the processed plurality of sensor data using cross-sectional analysis to obtain low level inference, wherein the cross-sectional analysis for the low level inference includes analyzing details of location, activity, temperature and physiology;

analyzing the processed plurality of sensor data, by a high level inference module, using a plurality of longitudinal analysis and Fourier analysis techniques based on the low level inference, domain knowledge and standard human metadata including mobility, proximity, activity of a human, wherein the domain knowledge includes health, shopping, retail and driving that are dynamically updated in a domain database, and wherein the plurality of longitudinal analysis and Fourier analysis techniques includes welch analysis, cross-spectrum analysis, Feature of interest (FOI) identification and time-series clustering, autocorrelation-based distance estimation and exponential smoothing, seasonal & non-seasonal models identification, ARIMA modelling, Hidden Markov models, Long short term memory (LSTM) along with the low level inference, the standard human metadata and the domain knowledge to provide insights for longitudinal tracking, prediction, and anomaly detection;

selecting a longitudinal analysis technique from the plurality of longitudinal analysis techniques for obtaining high level inference by the high level inference module connected to the domain database and a human metadata database, wherein the longitudinal analysis technique is selected based on expectation maximization techniques;

obtaining the domain adaptable human behavior inference using the unified platform based on the obtained low level inference and the high level inference, wherein for the health domain, the plurality of sensors including accelerometer, gyroscope, barometer, photoplethysmograph (PPG) obtains the domain adaptable human behavior inference corresponding to cardiac care pathway for patients, the low level inference obtained are Metabolic Equivalents (MET) values, heart rate, breathing-rate, breathing power and the high level inference obtained is computational model of cardiac fatigue per session of activity or cardiac care, wherein for the health domain, the plurality of sensors including passive infrared (PIR) sensors, door contact sensors and pill-box sensors obtains the domain adaptable human behavior inference corresponding to ambient assisted living for geriatric subjects, the low level inference obtained are daily and weekly routine of the geriatric subjects and the high level inference obtained is mild cognitive impairment detection among the geriatric subjects, wherein for a transportation domain, the plurality of sensors including Global Positioning System (GPS), inertial sensors obtains the domain adaptable human behavior inference corresponding to driving behavior understanding for transportation, the low level inference obtained are a lateral velocity and a jerk and the high level inference obtained is rash driving details, wherein for the transportation domain, the plurality of sensors including photoplethysmograph (PPG), accelerometer, gyroscope, barometer obtains the domain adaptable human behavior inference corresponding to ubiquitous journey recognition, the low level inference obtained is a vehicle recognition and the high level inference obtained is ubiquitous journey recognition; and displaying the unified domain adaptable human behavior inference on a unified display module based on a user query as only the low level inference or only the high level inference or both the low level inference and the high level inference, wherein for the transportation domain, the user query corresponds to if a driver is driving rash, then a system displays in confirmation along with the lateral velocity and the jerk, wherein the unified platform provides a unified low level inference and a high level inference of the domain adaptable human behaviour inference across multiple domains including the health, the retail and the transportation, and wherein an output module is configured to a set of Application Programming Interface (API) or service for user applications to interface with the unified platform to connect with the unified display module.

2. The method of claim 1, wherein processing the received sensor data to the standard format comprises the time series format using linear, non-linear interpolation and phase removing filters.

3. The method of claim 1, wherein standard human metadata including the mobility, the proximity, the activity for the human is dynamically updated in the human metadata database.

4. The method of claim 1, wherein Fourier analysis techniques is performed using sliding window to identify shift in frequency domain.

5. A system for obtaining unified domain adaptable human behaviour inference using a unified platform comprising:
a memory storing instructions and one or more modules;
a database;
one or more communication or input/output interfaces; and
one or more hardware processors coupled to the memory via the one or more communication interfaces, wherein the one or more hardware processors are configured by the instructions to execute the one or more modules comprising:

a input module for receiving a plurality of sensor data using a plurality of sensors, wherein the plurality of sensor data is in one or more sensor data formats, wherein the plurality of sensors includes wearable sensors, infrastructure sensors, near field sensors, infrared sensors, Near-Field Communication (NFC) sensors and soft sensors and wherein the plurality of sensors comprises databases comprising details regarding one or more users;

a pre-processor for processing the received plurality of sensor data to a time-series format;

a low level inference module for analyzing the processed plurality of sensor data using cross-sectional analysis to obtain low level inference, wherein the cross-sectional analysis for the low level inference includes analyzing details of location, activity, temperature and physiology;

a high level inference module for analyzing the processed plurality of sensor data using a plurality of longitudinal analysis and Fourier analysis techniques based on the low level inference, domain knowledge and standard human metadata including mobility, proximity, activity of a human, wherein the domain knowledge includes health, shopping, retail and driving that are dynamically updated in a domain database, wherein the plurality of longitudinal analysis and Fourier analysis techniques includes welch analysis, cross-spectrum analysis, Feature of interest (FOI) identification and time-series clustering, auto-correlation-based distance estimation and exponential smoothing, seasonal & non-seasonal models identification, ARIMA modelling, Hidden Markov models, Long short term memory (LSTM) along with the low level inference, the standard human metadata and the domain knowledge to provide insights for longitudinal tracking, prediction, and anomaly detection, and selecting a longitudinal analysis technique from the plurality of longitudinal analysis techniques for obtaining high level inference by the high level inference module connected to the domain database and a human metadata database, wherein the longitudinal analysis technique is selected based on expectation maximization techniques;

obtaining the domain adaptable human behavior inference using the unified platform based on the obtained low level inference and the high level inference, wherein for the health domain, the plurality of sensors including accelerometer, gyroscope, barometer, photoplethysmograph (PPG) obtains the domain adaptable human behavior inference corresponding to cardiac care pathway for patients, the low level inference obtained are Metabolic Equivalents (MET) values, heart rate, breathing-rate, breathing power and the high level inference obtained is computational model of cardiac fatigue per session of activity or cardiac care, wherein for the health domain, the plurality of sensors including passive infrared (PIR) sensors, door contact sensors and pill-box sensors obtains the domain adaptable human behavior inference corresponding to ambient assisted living for geriatric subjects, the low level inference obtained are daily and weekly routine of the geriatric subjects and the high level inference obtained is mild cognitive impairment detection among the geriatric subjects, wherein for a transportation domain, the plurality of sensors including Global Positioning System (GPS), inertial sensors obtains the domain adaptable human behavior inference corresponding to driving behavior understanding for transportation, the low level inference obtained are a lateral velocity and a jerk and the high level inference obtained is rash driving details, wherein for the transportation domain, the plurality of sensors including photoplethysmograph (PPG), accelerometer, gyroscope, barometer obtains the domain adaptable human behavior inference corresponding to ubiquitous journey recognition, the low level inference obtained is a vehicle recognition and the high level inference obtained is ubiquitous journey recognition; and a unified display module for displaying the obtained human behavior inference based on a user query as only the low level inference or only the high level inference or both the low level inference and the high level inference, wherein for the transportation domain, the user query corresponds to if a driver is driving rash, then the system displays in confirmation along with the lateral velocity and the jerk, wherein the unified platform provides a unified low level inference and a high level inference of the domain adaptable human behaviour inference across multiple domains including the health, the retail and the transportation, and wherein an output module is configured to a set of Application Programming Interface (API) or service for user applications to interface with the unified platform to connect with the unified display module.

6. One or more non-transitory machine readable information storage mediums comprising one or more instructions which when executed by one or more hardware processors cause:

receiving a plurality of sensor data using a plurality of sensors, wherein the plurality of sensor data is in one or more sensor data formats, wherein the plurality of sensors includes wearable sensors, infrastructure sensors, near field sensors, infrared sensors, Near-Field Communication (NFC) sensors and soft sensors and wherein the plurality of sensors comprises databases comprising details regarding one or more users;

processing the received plurality of sensor data to a time-series format;

analyzing the processed plurality of sensor data using cross-sectional analysis to obtain low level inference, wherein the cross-sectional analysis for the low level inference includes analyzing details of location, activity, temperature and physiology;

analyzing the processed plurality of sensor data, by a high level inference module, using a plurality of longitudinal analysis and Fourier analysis techniques based on the low level inference, domain knowledge and standard human metadata including mobility, proximity, activity of a human, wherein the domain knowledge includes health, shopping, retail and driving that are dynamically updated in a domain database, and wherein the plurality of longitudinal analysis and Fourier analysis techniques includes welch analysis, cross-spectrum analysis, Feature of interest (FOI) identification and time-series clustering, autocorrelation-based distance estimation and exponential smoothing, seasonal & non-seasonal models identification, ARIMA modelling, Hidden Markov models, Long short term memory (LSTM) along with the low level inference, the standard human metadata and the domain knowledge to provide insights for longitudinal tracking, prediction, and anomaly detection;

selecting a longitudinal analysis technique from the plurality of longitudinal analysis techniques for obtaining high level inference by the high level inference module connected to the domain database and a human metadata database, wherein the longitudinal analysis technique is selected based on expectation maximization techniques;

obtaining the domain adaptable human behavior inference using a unified platform based on the obtained low level inference and the high level inference, wherein for the health domain, the plurality of sensors including accelerometer, gyroscope, barometer, photoplethysmograph (PPG) obtains obtaining the domain adaptable human behavior inference corresponding to cardiac care pathway for patients, the low level inference obtained are Metabolic Equivalents (MET) values, heart rate, breathing-rate, breathing power and the high level inference obtained is computational model of cardiac fatigue per session of activity or cardiac care, wherein for the health domain, the plurality of sensors including passive infrared (PIR) sensors, door contact sensors and pill-box sensors are used for obtains the domain adaptable human behavior inference corresponding to ambient assisted living for geriatric subjects, the low level inference obtained are daily and weekly routine of the geriatric subjects and the high level inference obtained is mild cognitive impairment detection among the geriatric subjects, wherein for a transportation domain, the plurality of sensors including Global Positioning System (GPS), inertial sensors obtains the domain adaptable human behavior inference corresponding to driving behavior understanding for transportation, the low level inference obtained are a lateral velocity and a jerk and the high level inference obtained is rash driving details, wherein for the transportation domain, the plurality of sensors including photoplethysmograph (PPG), accelerometer, gyroscope, barometer obtains the domain adaptable human behavior inference corresponding to ubiquitous journey recognition, the low level inference obtained is a vehicle recognition and the high level inference obtained is ubiquitous journey recognition; and displaying the unified domain adaptable human behavior inference on a unified display module based on a user query as only the low level inference or only the high level inference or both the low level inference and the high level inference, wherein for the transportation domain, the user query corresponds to if a driver is driving rash, then a system displays in confirmation along with the lateral velocity and the jerk, wherein the unified platform provides a unified low level inference and a high level inference of the domain adaptable human behaviour inference across multiple domains including the health, the retail and the transportation, and wherein an output module is configured to a set of Application Programming Interface (API) or service for user applications to interface with the unified platform to connect with the unified display module.

7. The one or more non-transitory machine readable information storage mediums of claim 6, wherein processing the received sensor data to the standard format comprises the time series format using linear, non-linear interpolation and phase removing filters.

8. The one or more non-transitory machine readable information storage mediums of claim 6, wherein standard human metadata including the mobility, the proximity, the activity for human is dynamically updated in the human metadata database.

9. The one or more non-transitory machine readable information storage mediums of claim 6, wherein Fourier analysis techniques is performed using sliding window to identify shift in frequency domain.

* * * * *